United States Patent [19]
Chen

[11] Patent Number: 5,250,057
[45] Date of Patent: * Oct. 5, 1993

[54] ANASTOMOTIC DEVICE

[76] Inventor: Fusen H. Chen, 12 Vernon La., Thompson, Conn. 06277

[*] Notice: The portion of the term of this patent subsequent to Jun. 23, 2009 has been disclaimed.

[21] Appl. No.: 902,210

[22] Filed: Jun. 22, 1992

Related U.S. Application Data

[63] Continuation-in-part of Ser. No. 735,950, Jul. 25, 1991, Pat. No. 5,123,908, which is a continuation-in-part of Ser. No. 629,608, Dec. 18, 1990, Pat. No. 5,089,008, which is a continuation-in-part of Ser. No. 472,209, Jan. 26, 1990, Pat. No. 4,997,439, which is a continuation-in-part of Ser. No. 303,326, Jan. 26, 1989, Pat. No. 4,930,502.

[51] Int. Cl.⁵ .............................................. A61B 17/00
[52] U.S. Cl. ..................................... 606/153; 606/154
[58] Field of Search ................................. 606/153, 154

[56] References Cited

U.S. PATENT DOCUMENTS

| | | | |
|---|---|---|---|
| 3,990,434 | 11/1976 | Free | 606/153 |
| 4,523,592 | 6/1985 | Daniel | 606/153 |
| 4,693,249 | 9/1987 | Schenck et al. | 606/153 |
| 4,747,407 | 5/1988 | Liu et al. | 606/153 |

Primary Examiner—Stephen C. Pellegrino
Assistant Examiner—Gary Jackson
Attorney, Agent, or Firm—Morris Kaplan

[57] ABSTRACT

An anastomotic device of a pair of telescopically and frictionally locked annuli which each have a plurality of spaced retaining pins that each project from a respective outer wall of the annuli and are adapted to pierce a lumen wall to be joined, extend axially within said lumen wall and into the body of the opposed lumen wall.

6 Claims, 1 Drawing Sheet

1

ANASTOMOTIC DEVICE

CROSS-REFERENCE TO RELATED APPLICATIONS

This application is a continuation-in-part of application Ser. No. 07/735,950, filed Jul. 25, 1991, now U.S. Pat. No. 5,123,908, which is a continuation-in-part of application Ser. No. 07/629,608, filed Dec. 18, 1990, now U.S. Pat. No. 5,089,008, which is a continuation-in-part of application Ser. No. 07/472,209, filed Jan. 26, 1990, now U.S. Pat. No. 4,997,439, which, in turn, is a continuation-in-part of application Ser. No. 07/303,326, filed Jan. 26, 1989, now U.S. Pat. No. 4,930,502.

TECHNICAL FIELD

The present invention relates to the surgical joining of tubular structures and especially in the gastro-intestinal system after resection.

BACKGROUND OF THE INVENTION

The use of anastomotic devices for clamping and suturing is well known in the medical art. See, for instance, U.S. Pat. Nos. 2,638,901 (Sugarbaker); 3,254,650 (Collito); 4,233,981 (Schomacher); 4,294,255 (Geroc); 4,523,592 (Daniel); 4,657,019 (Walsh et al.); 4,693,249 (Schenck et al.); 4,747,407 (Liu et al.); and 4,757,407 (Liv et al.).

These and other patents are discussed in the referenced parent application files, the disclosures of which applications are incorporated herein by reference.

Prior art devices of the type are not fully satisfactory for at least some of the reasons that:

the device comprises a clamping means that requires a relatively large contact area with the tissue or body structure;

the device requires eversion of, and clamping pressure on, the anastomosed parts that may be causative of necrosis or at least result in severely diminished blood flow and a prolonged period for healing;

the device is of undue size and weight;

the device is awkward to use, in contradistinction to efficient surgical procedure; and the device is relatively sophisticated with respect to manufacture and use.

An anastomotic device that is particularly directed to surgical joining of the intestine is the VATRAC ® Bar produced by the Davis & Geck Medical Device Division of the American Cyanamid Company. This device is relatively large, requires sophisticated handling, partial eversion of the intestinal parts and clamping thereof.

SUMMARY OF THE INVENTION

The present invention is directed to an improved surgical device that is especially useful for intestinal joinder and is: mechanically simple and inexpensive to manufacture; easy to use to thus facilitate efficient surgical procedure; provides for minimal device-to-body structure area of contact; does not require eversion or clamping of the lumen walls; provides a telescopic-friction-interlock of annular parts which results in a simplified structure of reduced mass and which parts are each provided with spaced retaining pins that are each adapted to effect anastomosis by impaling a respective first lumen wall, extend therethrough in the general luminal axis direction and subsequently impale an opposed lumen wall to effect surgical joinder and the device is disposed within the lumen.

DETAILED DESCRIPTION OF THE INVENTION

Figure 2:
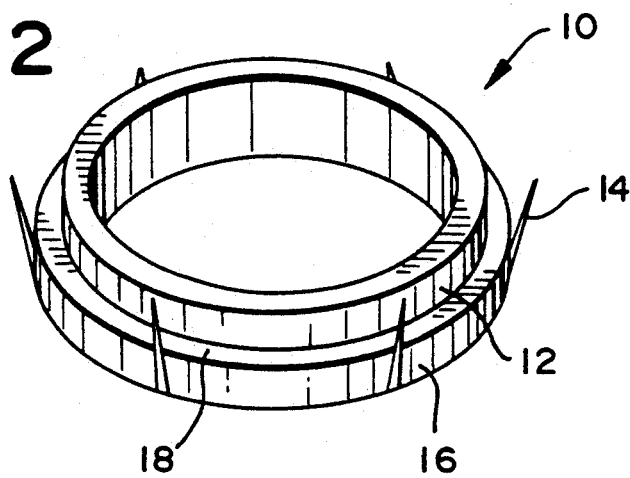
FIG. 2 is a perspective of the inner annulus.

Referring to the drawings which illustrate a preferred embodiment of the invention and wherein like numerals indicate like elements of structure, there is shown in FIG. 2 an annular member 10 having an outer wall portion 12 of diminished thickness and a series of spaced retaining pins 14 that each project outwardly at about 10° from the outer end portion of wall section 16 of said outer wall and extend to beyond the shoulder 18 that terminates the diminished wall portion 12.

Figure 1:
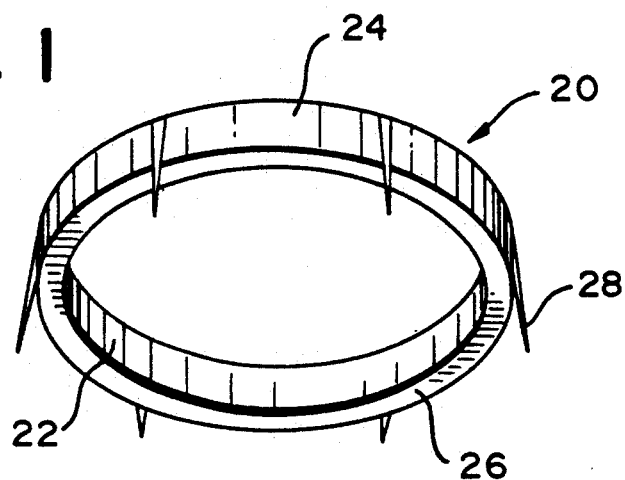
FIG. 1 is a perspective view of the outer annulus of the device.

FIG. 1 discloses an annular member 20 having an inner wall 22, an outer wall 24, and an end wall 26.

Figure 3:
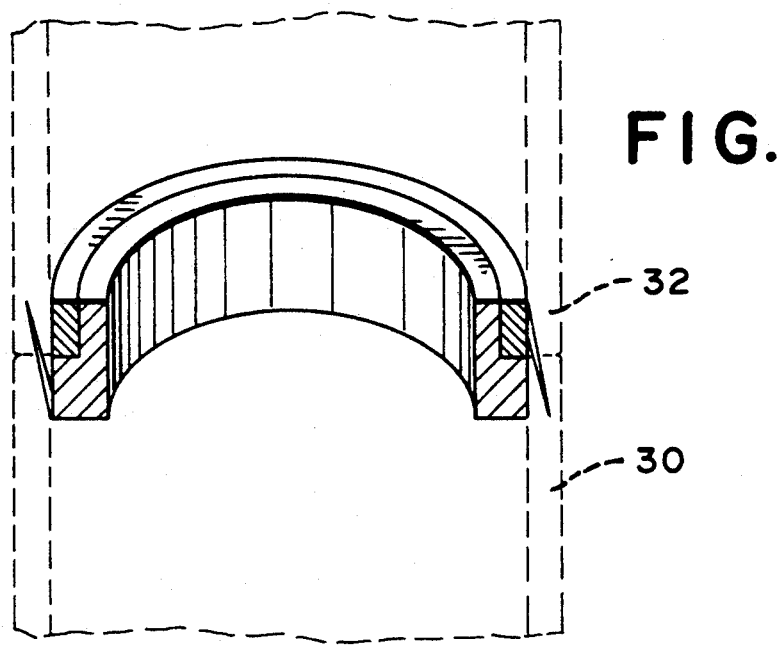
FIG. 3 is a sectional, elevational view of the device in operative association of its parts and functional with respect to anastomosed structure shown in broken lines, parts of retaining pins being omitted for clarity.

As shown in FIG. 3, the wall portion 12 is dimensioned to be telescopically received and frictionally locked in annulus 20, with said end wall 26 abutting shoulder 18 and the outer surfaces 16, 24 presenting in effect a continuous wall of generally uniform diameter; but for said retaining pins 14, and corresponding pins 28 that are integral with annulus 20, project outwardly at about 10° from an end section of wall 24 and extend beyond the transverse plane of mating of said end wall 26 and shoulder 18.

FIG. 3 discloses the novel and improved device in functional relationship with anastomosed lumens 30, 32 (shown in broken lines), whose intima are opposed and aligned. For purposes of clarity, not all retainer pin structure is disclosed, and the parts are dimensionally exaggerated.

In use, the annuli are arranged for operative association so that the axially opposed retaining pins are in alternate relationship with one another, and a separate annulus of the device, at its non-piercing end, is inserted into a respective one of the lumens until the pins reach the desired point of impalement entry. The respective lumen is then retracted to effect impalement on the associated retaining pins to the extent that each lumen wall end associates and aligns with its respective end wall 18 or 26. As shown, the retaining pins lie within the respective lumen walls except for end portions which extend through the respective ends of the lumen walls and are adapted to extend into and within the opposed lumen wall. The annuli are then telescopically joined whereby to be frictionally locked and the free ends of the retaining pins entered into the opposed lumen. Means may be provided to either visually or mechanically effect such alternate disposition of the retaining pins.

The retaining pins may vary in configuration with a view to lumen size and to enhancing lumen retention, and the number of pins utilized may vary in accordance with specific need.

The materials of fabrication are flexible, compatible with that of the human body, biodegradable and biofragmentable and may be treated or coated in order to control the time of material dissolution and fragmentation, as is known in the art. However, dissolution is not a problem since the device is primarily disposed within the intestinal tract and will be naturally eliminated.

The anastomotic embodiment of the invention described and illustrated is of relatively small mass, simplistic in structure and mechanical association, is significantly of minimal radial extension and, in use, requires no lumen wall eversion or distortion.

The embodiment shown and described is only illustrative of the present invention and is not to be construed as delimitive thereof, since once appraised of the invention, changes in structure would be readily apparent to one skilled in the art. Hence, the present invention includes all modifications of the structure encompassed within the spirit and scope of the following claims.

I claim:

1. Means for joining tubular elements, especially an anastomotic device for the intestinal tract, comprising:
   first and second annular members;
   said first member (10) having a diminished wall thickness portion (12) that is dimensioned to be telescopically received, in frictional retention, within the second (20) of said members;
   said diminished wall thickness portion (12) extending axially from one end of said first member (10);
   the outer walls of said members in such telescopic assembly presenting a generally continuous outer wall (16, 24) of generally uniform diameter; and
   pin means integral with and extending from said outer wall of said assembly of annular members adapted to retain said tubular elements in a non-everted or overlapped, joined relationship.

2. Means as in claim 1, wherein the outer wall of said diminished wall thickness portion terminates at a shoulder (18) configuration and the telescopically associated end (26) of said second member abuts said shoulder.

3. Means as in claim 1, wherein:
   said retaining pin means comprise a first plurality (14) of spaced pins that each projects outwardly from the outer wall of the first member, at the outer end section removed from the diminished wall thickness portion (12), and extends to beyond the transverse plane of mating of the outer walls of said first and second members; and
   each of said pins is dimensioned and configured to pierce a first body of said joined tubular elements, extend in general axial direction within the wall of said first tubular element and into the body of the opposed second tubular element.

4. Means as in claim 3, wherein:
   said retaining means further comprise a second plurality (28) of spaced retaining pins that dimensionally and configuratively correspond to said first plurality of pins; and
   each pin of said second plurality projects outwardly from the outer wall of the second annular member (20), at an end section removed from the lead end receiving the telescopically associated first member, and extends to beyond said transverse plane of mating;
   whereby each pin of said second plurality is adapted to pierce the body of said second tubular element, extend generally axially within the wall of said second element and into the body of the opposed first tubular element.

5. Means as in claim 4, wherein in the assembled annuli, each pin of each said plurality lies intermediate pins of the opposed plurality of pins.

6. Means as in claim 2, wherein:
   said retaining means comprise a first plurality of spaced pins, each said pin projecting outwardly from an outer end section of the outer wall of said first member and extending to beyond the transverse plane of mating of the outer walls of said first and second members;
   each said first plurality of pins being dimensioned and configured to pierce a first body of said tubular elements to be joined, extend in general axial direction within the wall of said first tubular part and into the body of the opposed second tubular element to be joined; and
   said retaining means further comprise a second plurality of spaced pins that dimensionally and configuratively correspond to said first plurality of pins, each said second plurality of pins projects outwardly from an outer end section of the outer wall of the second annular member and extends to beyond said transverse plane of mating,
   whereby each pin of said second plurality is adapted to pierce the body of said second tubular element, extend generally axially within the wall of said second element and into the body of the opposed first tubular element.

* * * * *